(12) United States Patent
Komi

(10) Patent No.: US 6,508,758 B2
(45) Date of Patent: Jan. 21, 2003

(54) MANUAL CONTROL PART OF ENDOSCOPE

(75) Inventor: Shuji Komi, Omiya (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 39 days.

(21) Appl. No.: 09/770,227

(22) Filed: Jan. 29, 2001

(65) Prior Publication Data

US 2001/0018551 A1 Aug. 30, 2001

(30) Foreign Application Priority Data

Feb. 3, 2000 (JP) .................................... 2000-026481

(51) Int. Cl.$^7$ ................................................ A61B 1/00
(52) U.S. Cl. ....................................... 600/131; 600/197
(58) Field of Search ................................ 600/131, 197, 600/101

(56) References Cited

U.S. PATENT DOCUMENTS 4,425,909 A * 1/1984 Rieser ........................... 600/197
4,598,698 A * 7/1986 Siegmund ..................... 600/131
5,088,819 A * 2/1992 Storz ........................... 356/241.1

FOREIGN PATENT DOCUMENTS

JP          57-109804          7/1982

* cited by examiner

Primary Examiner—Linda C. M. Dvorak
Assistant Examiner—Kenneth G Schopfer
(74) Attorney, Agent, or Firm—Birch, Stewart, Kolasch & Birch, LLP

(57) ABSTRACT

In a manual control part of the present invention, a transverse section of a grip is formed in such a manner that two arches with centers inside the grip and with different radii of curvature are connected with each other. The radius of curvature of one arch the finger pads of an operator touch is larger than that of the other arch the palm of the operator touches. In addition, a part of the grip formed by the arch the finger pads touch is thinner than a part formed by the arch the palm touches.

5 Claims, 5 Drawing Sheets

F I G. 2
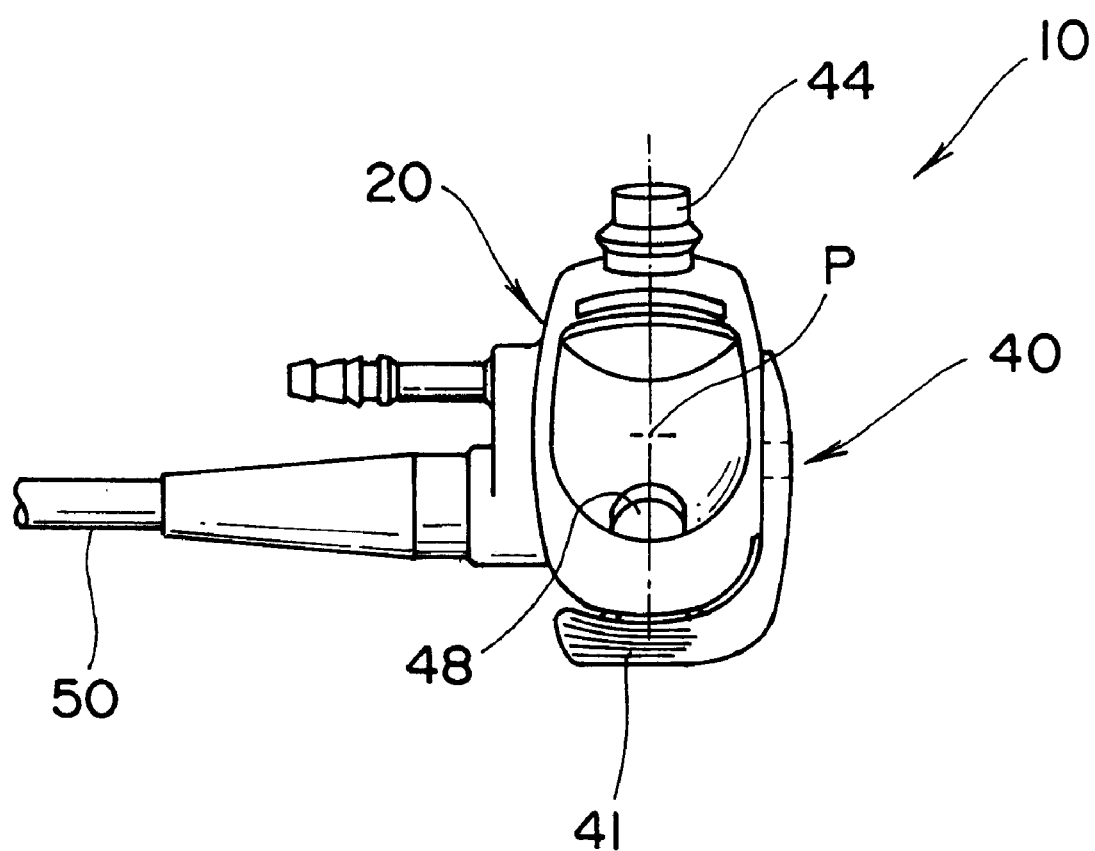

F I G. 5
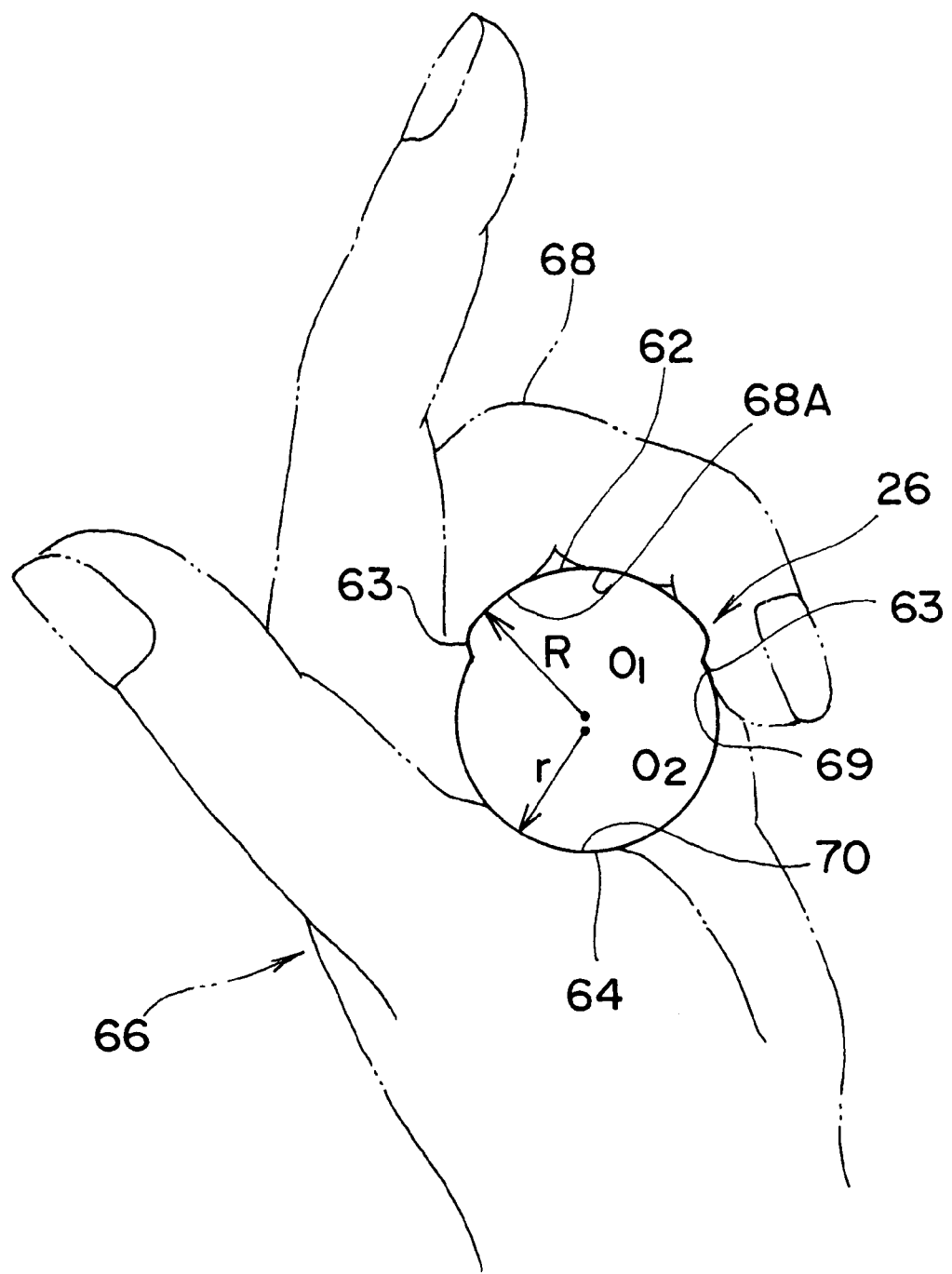

MANUAL CONTROL PART OF ENDOSCOPE

BACKGROUND OF THE INVENTION

1. Field of the Invention

The present invention generally relates to a manual control part of an endoscope, more particularly to a manual control part of an endoscope with a grip which can be easily held by an operator in one hand.

2. Description of Related Art

A manual control part of an endoscope for medical use comprises a grip held by an operator in one hand, and a control part with a knob for curving control and air and water supply buttons. Grips with various shapes have been suggested to be easily held.

Japanese Utility Model Application Laid-Open No. 57-109804 discloses a grip in which the middle part between both sides is thinner than at least one of the sides. It exemplifies a grip whose transverse section is a trapezoid in which one side the fingers of the operator touch is thick and the thickness is gradually reduced toward the other side the palm of the operator touches. Moreover, it also exemplifies a grip in which the middle part and the side the palm touches are of the same thickness and thinner than the side the fingers touch.

In above-mentioned Japanese Utility Model Application Laid-Open No. 57-109804, however, it is difficult for the operator to contact the fingers and the palm with the surface of the grip since the transverse section of the grip is substantially quadrilateral, and thus the grip cannot be securely held.

In addition, the side the fingers touch is thicker than the other parts, and thus the palm may lose contact with the grip. Therefore, a satisfactory grip cannot be guaranteed.

SUMMARY OF THE INVENTION

The present invention has been developed in view of the above-described circumstances, and has as its object the provision of a manual control part of the endoscope with a grip that can be firmly held.

In order to achieve the above-described object, the present invention is directed to a manual control part of an endoscope with a grip held by an operator in one hand, wherein: a transverse section of the grip is formed in such a manner that first and second arches are connected with one another, the first and second arches having centers inside the grip and radii of curvature different from one another, the first arch touching pads of fingers of the hand, the second arch touching a palm of the hand; the radius of curvature of the first arch is larger than the radius of curvature of the second arch; and a part of the grip formed by the first arch is thinner than a part of the grip formed by the second arch.

According to the invention, since the transverse section of the grip is formed in such a manner that the two arches with centers inside the grip and with the different radii of curvature are connected with each other, the fingers and the palm can be firmly contacted with the surface of the grip. Moreover, the radius of curvature of one arch the finger pads of the hand touch is larger than that of the other arch the palm of the hand touches, and the part of the grip formed by the arch the finger pads touch is thinner than the part formed by the arch the palm touches. Thus, when the finger pads are firmly contacted with the arch at the one side, the palm can be naturally contacted firmly with the arch at the other side. Therefore, the grip of the present invention can be securely held by the operator.

Preferably, a circle including the arch the palm touches is inside a circle including the arch the finger pads touch. Thus, the section area of the grip is small and the manual control part can be small.

Preferably, a step is formed at a boundary between the two arches as a stopper for fingertips. Thus, the grip can be more easily held.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein:

FIG. 2 is a rear view of the manual control part in FIG. 1 along the line 2—2 viewed from FIG. 1;

FIG. 5 is an explanatory view of the grip of the manual control part when being held.

DETAILED DESCRIPTION OF THE PREFERRED EMBODIMENT

Hereunder a preferred embodiment of a manual control part of an endoscope of the present invention will be described in accordance with the accompanied drawings.

Figure 1:
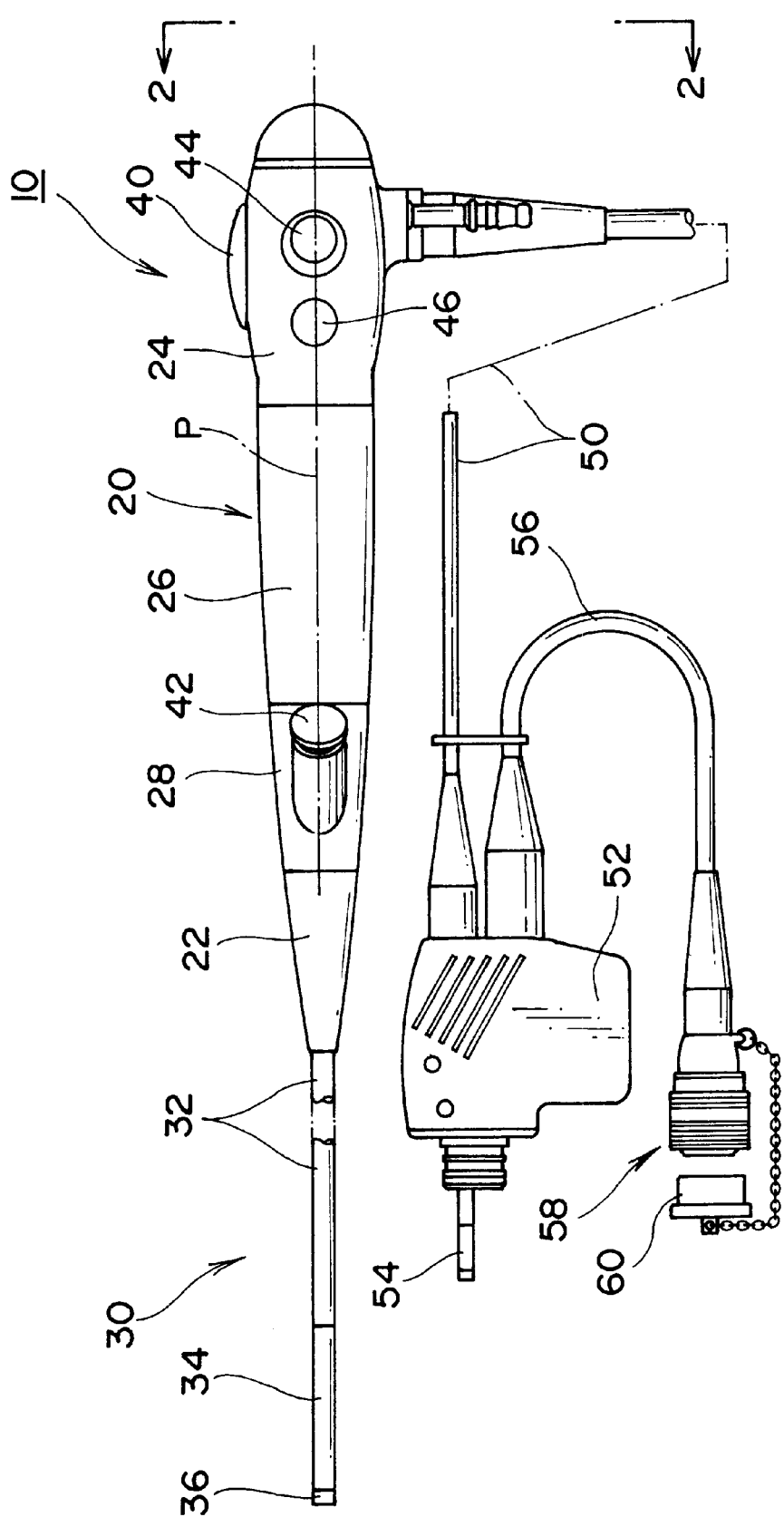
FIG. 1 is a top view of an endoscope for medical use to which a manual control part of an endoscope of the present embodiment is applied.

FIG. 1 is a top view of an endoscope 10 for medical use to which the manual control part of the endoscope of the present embodiment is applied.

The endoscope 10 in FIG. 1 has a manual control part 20, and an insertion part 30 which is inserted into an abdominal cavity is connected with a top joint 22 of the manual control part 20. Although not shown, members such as a cable, a light guide, and respective channels are inserted through the insertion part 30, which comprises a soft portion 32, a curved portion 34, and a top hard portion 36. In the insertion part 30, the curved portion 34 is connected, via an angle control wire (not shown) inserted into the soft portion 32, with an angle control knob 40 shown in FIG. 2 which is provided to a control part 24 of the manual control part 20. Thus, when the angle control knob 40 is operated by an operator who holds the grip 26 of the manual control part 20 with the operator's left/right hand, the curved portion 34 is bent, and the top hard portion 36 is directed in a desired direction. The reference number 42 is assigned to a forceps hole which is provided to a forceps division 28 that is disposed between the top joint 22 and the grip 26 of the manual control part 20. An associated medical tools such as a forceps and a snare are inserted into the insertion part 30 through the forceps hole 42.

Figure 3:
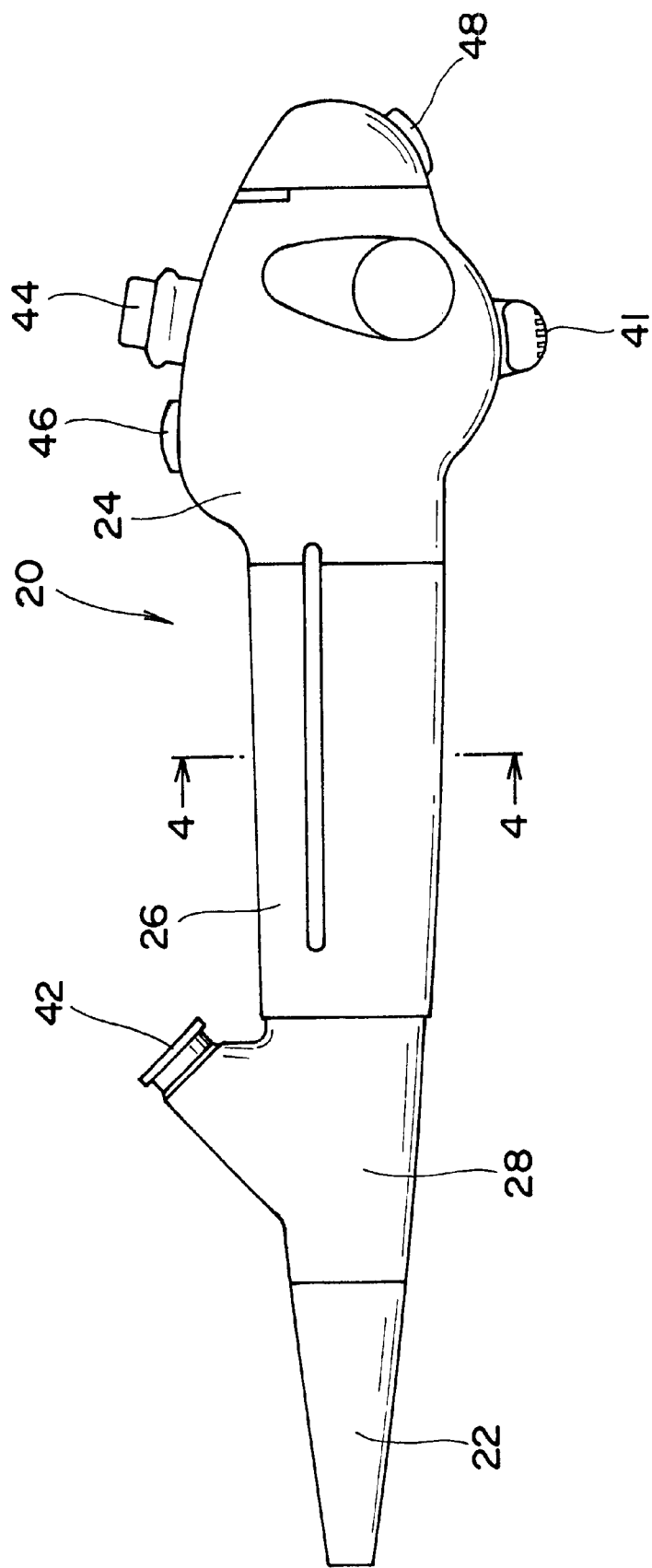
FIG. 3 is a side view of the manual control part in FIG. 1.

A suction button 44, and a freeze switch 46 are provided in a line on the top face of the control part 24 of the manual control part 20, while a VTR switch 48 is provided to the rear end part of the control part 24 as seen from FIGS. 2 and 3. The suction button 44, the freeze switch 46m, the VTR switch 48, and the angle control knob 40 are operated by the operator who holds the grip 26. For example, if the grip 26 is held by the operator's left hand, the VTR switch 48 and the angle control knob 40 are operated with the operator's left thumb, whereas the suction button 44 and the freeze switch 46 are operated with the operator's index finger. Hence, the grip 26 is held with the operator's three fingers except the thumb and the index finger.

In the endoscope 10 of the present invention, the forceps hole 42, the suction button 44, and. the freeze switch 46 are arranged directly above the central axis P of the manual control part 20, while a tab 41 of the angle control knob 40 is arranged directly below the central axis P as seen from FIGS. 1 and 2. Moreover, the VTR switch 48 is arranged between the central axis P and the tab 41. Therefore, the endoscope 10 as a whole can be operated in good balance with either of the operator's hands no matter that the manual control part 20 is held with the operator's left hand or right hand.

The control part 24 of the manual control part 20 is connected with a light guide connector 52 via a soft tube 50 through which a light guide is inserted. The light guide connector 52 is provided with a light guide stick 54 with which a light source device (not shown) is connected. The light guide connector 52 is also connected with an electric connector 58 via a flexible tube 56. The electric connector 58 is connected with an image processing unit (not shown) when using the endoscope 10, and is closed with a waterproof cap 60 when cleaning the endoscope 10 so as to block the cleaning liquid from the electric connector 58.

Figure 4:
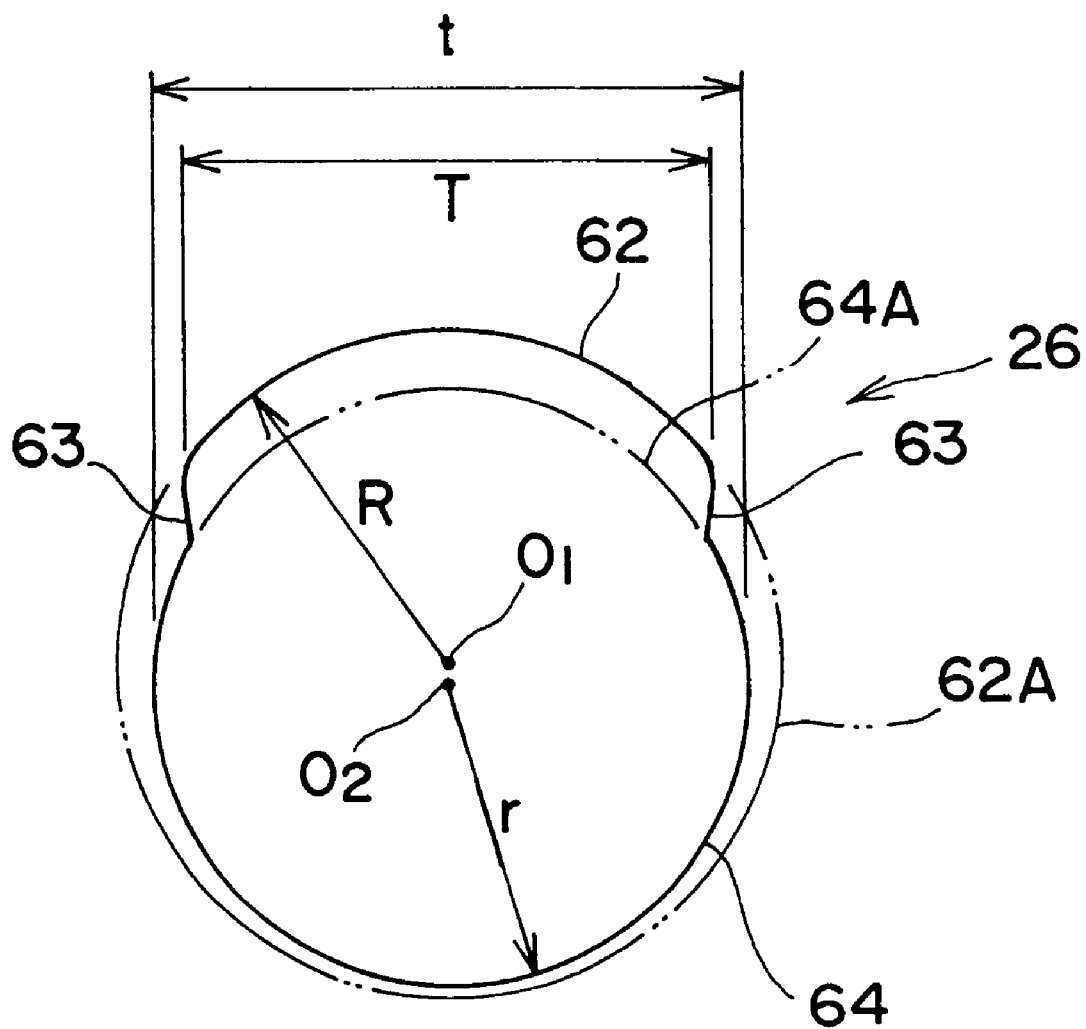
FIG. 4 is a section view of the grip of the manual control part along the line 4—4 in FIG. 3.

In order to improve its grip, the contour of the grip 26 of the present invention in transverse section is formed in such a manner that two arches with different radii of curvature R and r are connected with each other, the two arches having the centers of curvatures $O_1$ and $O_2$ at inside of the grip 26 as seen from FIG. 4. Moreover, the radius of curvature R of an arch 62 with which the respective finger pads 68A of three fingers (middle, third, and little fingers) 68 of a hand 66 illustrated by an alternate long and two short dashes line in FIG. 5 comes into contact is larger than the radius of curvature r of an arch 64 with which a palm 70 comes into contact. Also as seen from FIG. 4, a thickness T of the grip 26 formed by the arch 62 is thinner than a thickness t formed by the arch 64.

By forming the grip 26 in the shape as described above, since the contour shape of the grip 26 in transverse section is arched, the finger pads 68A of the hand 68 and the palm 70 of the hand 66 can be more easily contacted firmly with the outer peripheral face of the grip 26 when compared with the conventional grip which is rectangle in transverse section.

The grip 26 is made in such a manner that the radius of curvature R of the arch 62 with which the finger pads 68A of the fingers 68 of the hand 66 is larger than the radius of curvature r of the arch 64 with which the palm 70 comes into contact, while the thickness T of the grip 26 formed by the arch 62 is thinner than the thickness t of the grip 26 formed by the arch 64. Therefore, when firmly contacting the finger pads 68A of the fingers 68 with the arch 62 as shown in FIG. 5, the palm 70 naturally contacts with the arch 64 firmly. Therefore, the grip 26 of the present embodiment can be securely held by the operator with the operator's hand 66.

The grip 26 forms the arches 62 and 64, so that a circle 64A, which is indicated with an alternate two long and short dotted line in FIG. 4 and is formed by an extended part of the arch 64 is positioned within a circle 62A, which is indicated by the alternate two long and short dotted line in FIG. 4 and is formed by an extended part of the arch 62 as shown in FIG. 4. Therefore, the area of section of the grip 26 is smaller than the grip with an area of section of the circle 62A, and thus the manual control part 20 can be compact in size.

In the grip 26, a step 63 is formed at a boundary of the two arches 62 and 64. The step 63 is used as a stopper for fingertips 69 by contacting the fingertips 69 in FIG. 5 with the step 63. Hence, the grip 26 can be even better held.

In the present embodiment, the manual control part 20 of the endoscope 10 for medical use is explained; however, the present invention may also be applied to a manual control part for an industrial use without the forceps hole 42 and the suction button 44.

As described above, according to the manual control part of the endoscope of the present invention, the contour of the grip in transverse section is formed in such a manner that the two arches with different radii of curvature are connected with each other, the two arches having centers of the curvatures at inside of the grip. Moreover, according to the manual control part of the present invention, the radius of curvature of the arch at one side with which the finger pads of the hand comes into contact is larger than the counterpart of the arch at the other side with which the palm comes into contact, whereas the grip formed by the arch at the one side is thinner than the grip formed by the arch at the other side. Therefore, the present invention can provide a grip which can be securely held by the operator with the operator's hand.

According to the present invention, the arch of one side and the arch of the other side are formed so that the circle formed by the extended part of the arch at the other side of the grip is situated within a circle formed by the extended part of the arch at the one side of the grip. Thus, the area of the grip in section is smaller and the manual control part can be compact in size.

Further, according to the present invention, the stepped part which is used as a stopper for the fingertips is formed at the boundary of the two arches of the grip; thus the grip can be even more easily held.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. A manual control part of an endoscope with a grip held by an operator in one hand, wherein:

a transverse section of the grip is formed in such a manner that first and second arches are connected with one another, the first and second arches having centers inside the grip and radii of curvature different from one another, the first arch touching pads of fingers of the hand, the second arch touching a palm of the hand;

the radius of curvature of the first arch is larger than the radius of curvature of the second arch; and a part of the grip formed by the first arch is thinner than a part of the grip formed by the second arch.

2. The manual control part of the endoscope as set forth in claim 1, wherein a step is formed at a boundary between the first and second arches as a stopper for tips of the fingers.

3. The manual control part of the endoscope as set forth in claim 1, wherein a circle including the second arch is inside a circle including the first arch.

4. The manual control part of the endoscope as set forth in claim 3, wherein a step is formed at a boundary between the first and second arches as a stopper for tips of the fingers.

5. The manual control part of the endoscope as set forth in claim 1, wherein the manual control part includes a control part wherein the control part and the grip are arranged on a straight line along an insertion part.

* * * * *